United States Patent [19]

Clark et al.

[11] Patent Number: 4,457,894
[45] Date of Patent: Jul. 3, 1984

[54] SEMI-AUTOMATED AGGLUTINATION VIEWER FOR SEROLOGY TESTING

[76] Inventors: George H. Clark; Mary A. Clark, both of 3112 Del Rey Ave., Carlsbad, Ca. 92008

[21] Appl. No.: 353,510

[22] Filed: Mar. 1, 1982

[51] Int. Cl.³ .................... G01N 33/54; G01N 35/00
[52] U.S. Cl. ....................................... 422/73; 356/244; 356/246; 422/50; 422/63; 422/68; 422/104; 436/809; 435/300
[58] Field of Search ........................ 422/50, 68, 63, 73, 422/104; 356/244, 246; 436/809; 435/300

[56] References Cited

U.S. PATENT DOCUMENTS

| | | | |
|---|---|---|---|
| 3,488,156 | 1/1970 | Good et al. | 422/73 |
| 3,554,702 | 1/1971 | Shanbrom et al. | 422/68 |
| 3,876,379 | 4/1975 | Ghim | 422/73 |
| 4,099,881 | 7/1978 | Broek et al. | 356/244 |
| 4,226,503 | 10/1980 | Irazoqui et al. | 356/246 |

Primary Examiner—Michael S. Marcus
Attorney, Agent, or Firm—John H. Widdowson

[57] ABSTRACT

A semi-automated agglutination viewer comprising a housing having a top, a front panel, and a back. A rocker tray is rotatably supported by the housing. Power is supplied to a motor within the housing which, through intermeshing gears and a rocker arm interconnecting the gears and the tray, causes rocking of the tray. A method of serology testing comprising placing test slides on the rocker tray; adding a predetermined amount of a reagent and a test specimen to the slides; stirring the admixed reagent and test specimen; setting the controls on the length and speed of rocking of the rocker tray; and activating the rocking of the rocker tray.

4 Claims, 10 Drawing Figures

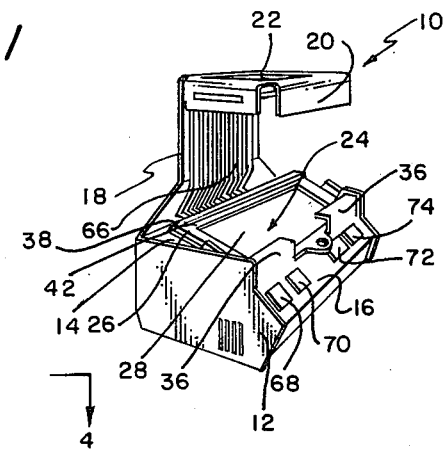
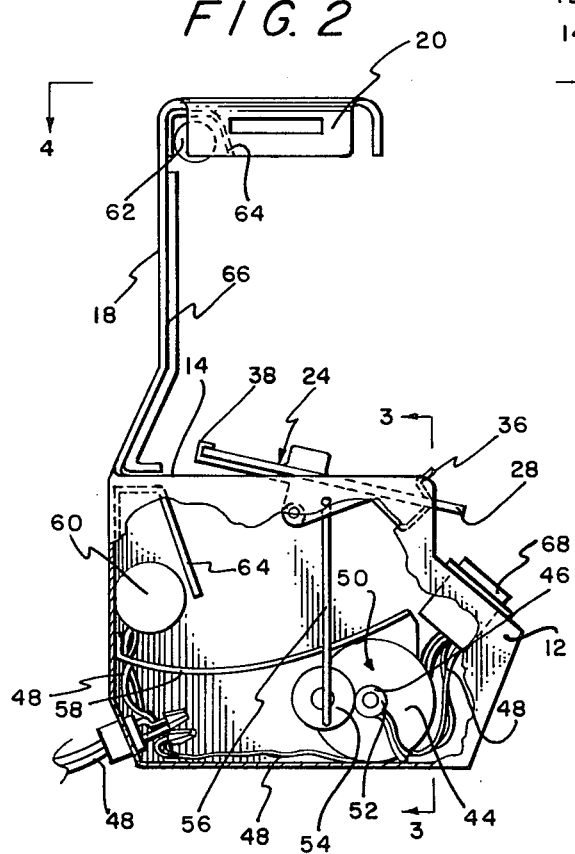
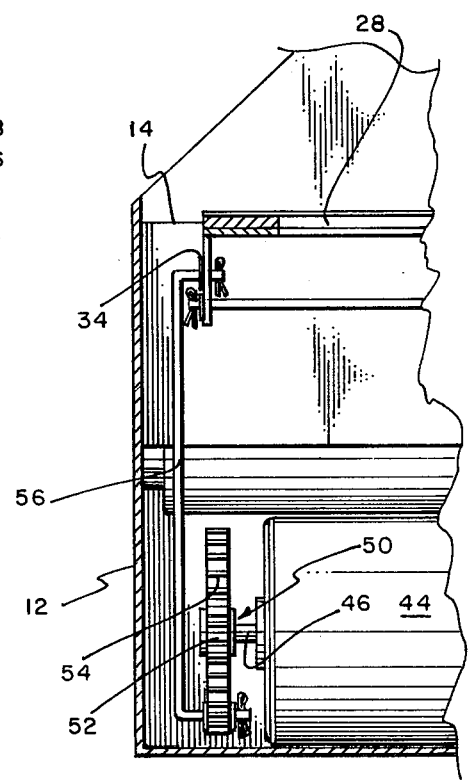
FIG. 1
FIG. 2
FIG. 3

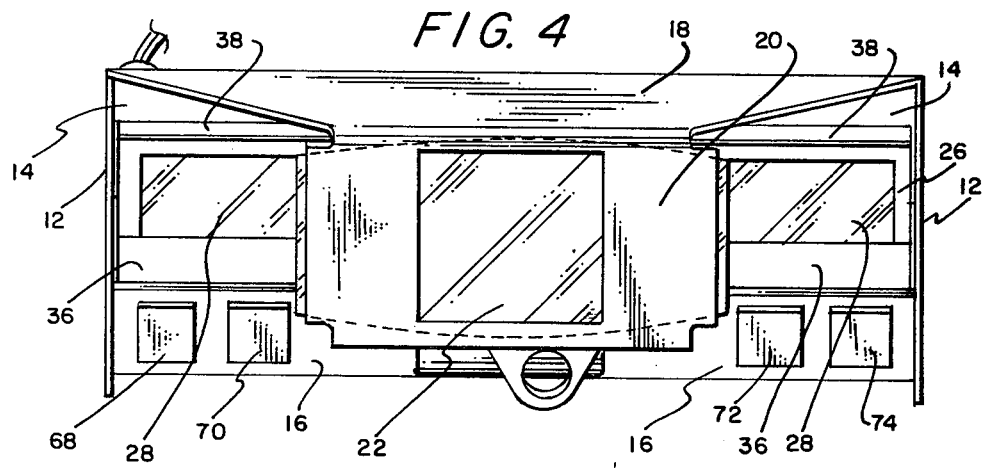
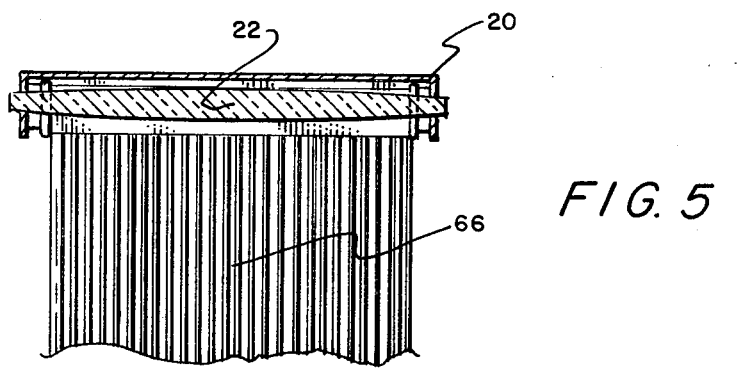
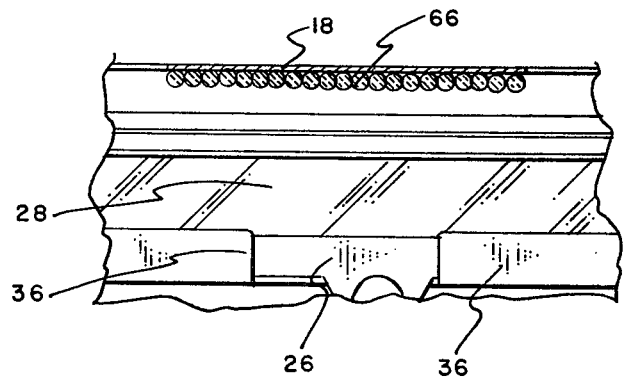

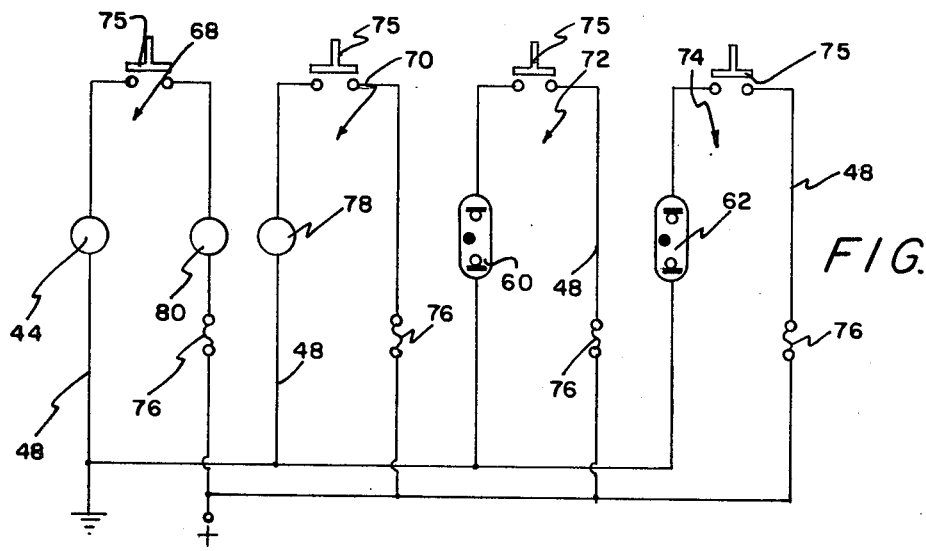
FIG. 7
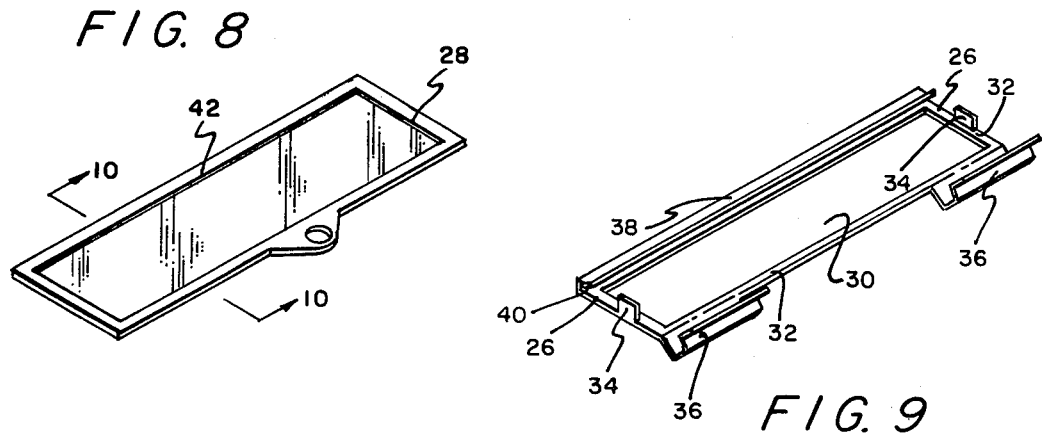
FIG. 8
FIG. 9
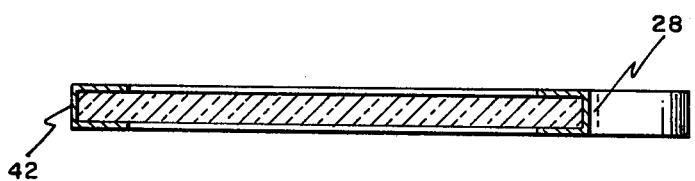
FIG. 10

SEMI-AUTOMATED AGGLUTINATION VIEWER FOR SEROLOGY TESTING

BACKGROUND OF THE INVENTION

1. Field of the Invention

This invention is related to agglutination. More specifically, this invention provides for a semi-automated agglutination viewer and a method of serology testing.

2. Description of the Prior Art

U.S. Pat. No. 3,876,379 by Ghim relates to a blood agglutination testing apparatus having a tray onto which a plurality of samples may be placed and the support moved in such a manner to mix the samples and reagents. U.S. Pat. No. 3,488,156 by Good et al also discloses an agglutination device wherein a plurality of samples may be subjected to motion for mixing and a light source provided so that light transmitted through the cups after agitation can be measured to determine whether agglutination has occured. U.S. Pat. No. 2,610,541 by Rowland, Jr., discloses a blood testing apparatus whereby light may be transmitted through the sample to the cathode of a photoelectric cell for measurement. None of the foregoing prior art teaches or suggests the particular agglutination viewer and method of serology testing of this invention.

SUMMARY OF THE INVENTION

This invention accomplishes its desired objects by providing a semi-automated agglutination viewer comprising a housing having a top and a front panel. A back is bound to the housing and generally perpendicularly extends therefrom with respect to the top thereof. A magnifying retainer means attaches to the back. Rocker tray means is rotatably supported by the housing within the top thereof, and a motor means having a motor shaft is housed within the housing. Power means electrically engages the motor means to supply power to same for rotating the motor shaft. Gear means engages the motor shaft for rotational power take-off therefrom. A rocker arm means pivotally attaches to the rocker tray means and is secured eccentrically to the gear means such as to produce vertical reciprocation on the rocker arm means from rotary power take-off from the gear means to cause rocking of the tray means. The method of serology testing comprises placing test slides on the rocker tray means; adding a predetermined amount of a reagent and a test specimen to the slides; stirring the admixed reagent and test specimen; setting timer means and speed control means for the respective length and speed of rocking of the rocker tray means; and activating the rocking of the rocker tray means.

It is an object of the invention to provide a novel semi-automated agglutination viewer and method of serology testing.

Still further objects of the invention reside in the provision of an agglutination view which can be easily transported, provides easy accessibility to the samples within a rocking tray, and is relatively inexpensive to manufacture.

These, together with the various ancillary objects and features which will become apparent as the following description proceeds, are attained by this invention, preferred embodiment being shown in the accompanying drawings, by way of example only, wherein:

BRIEF DESCRIPTION OF THE DRAWINGS

FIG. 1 is a perspective view of the invention;

FIG. 2 is a side elevational view of the invention with the internal components of the invention revealed;

FIG. 3 is a vertical view taken in direction of the arrows and along the plane of line 3—3 in FIG. 2;

FIG. 4 is a horizontal view taken in direction of the arrows and along the plane of line 4—4 in FIG. 2;

FIG. 5 is a vertical sectional view of magnifying retainer and a partial view of the back of the invention;

FIG. 6 is a horizontal sectional view of the back of the invention and a partial top plan view of the top of same;

FIG. 7 is the electrical diagram of the invention;

FIG. 8 is a perspective view of the snap-in sample handling tray;

FIG. 9 is a perspective view of the tray support for snapping in the sample handling tray; and FIG. 10 is a vertical sectional view of the tray taken in direction of the arrows and along the plane of line 10—10 in FIG. 8.

DETAILED DESCRIPTION OF THE INVENTION

Referring in detail now to the drawings, wherein like reference numerals designate similar parts throughout the various views, there is seen an agglutination viewer, generally illustrated as 10, comprising a housing 12 having a top 14 and a front panel 16. Upright back 18 is bound to the housing 12 and a magnifying retainer 20 having a magnifying lens 22 is attached essentially perpendicularly to the upright back 18.

Rocker tray means, generally illustrated as 24, is rotatably, pivotally supported by the housing 12 within the top 14 thereof. Rocker tray means 24 includes a rocker tray support 26 (see FIG. 9) rotatably supported by the housing 12 and a transparent sample handling tray 28 (see FIGS. 8 and 10) having an edge 42. Tray means 24 and tray 28 are constructed as illustrated such that in operation the handling tray 28 snaps into or snaps out of the rocker tray support 26.

Rocker tray support 26 comprises a transparent rocker base 30 (see FIG. 9) with a perimeter frame 32 having a pair of ears 34-34 integrally bound thereto for rotatably attaching the tray support 26 to the housing 12. A pair of flexible lips 36-36 protrudes from the frame 32. Tray support 26 also comprises a rocker tray back 38 defining a channel 40 (see FIG. 9) for receiving the edge 42 of the handling tray 28 when the same is snapped into the rocker tray support 26.

A motor 44 housing a shaft 46 is mounted in the housing 12 and is electrically engaged via conductors 48 to a power source for electrical conduction of energy to rotate the shaft 46. Gear means, generally illustrated as 50, is connected to the shaft 46 for rotational power take-off therefrom. Gear means 50 preferably comprises shaft gear 52 bound to shaft 46 and intermeshes with a rocker arm gear 54. Rocker arm 56 is attached to at least one ear 34 and is secured eccentrically to rocker arm gear 54 such as to vertically reciprocate the rocker arm 56 from rotary power take-off from the rotating rocker arm gear 54 to cause rocking of the tray means 24.

The agglutination viewer 10 additionally comprises an essentially arcuate background 58 enclosed within and suported by the housing 12 above the motor 44 and the gear means 50. A lamp 60 is electrically engated to the power source by conductors 48 and is supported within and by the housing 12. A fluorescent lamp 62 is also electrically engaged to the power source by conductors 48 and is positioned (see FIG. 2) in the corner of the adjoining point of the upright back 18 and the magnifying retainer means 20. A light shield 64 is situated over the lamp 60 and the fluorescent lamp 62.

A usual fiber optics systems means, generally illustrated as 66, is attached to the upright back 18 and functions in its usual manner in operation of the method of the invention.

A timer means 68 electrically connects to the power source by conductors 48 and selectively engages the motor 44 to control the length of the rocking time of the tray means 24. A speed control means 70 also electrically engages the power source by conductors 48 and also selectively engages the motor 44 to control the speed with which the rocker tray means 24 moves in the rocking mode via the gear means 50 and the rocking arm 56. Reflected lamp source control means 72 and reflected fluorescent lamp source means 74 both yet further electrically engage the power source through conductors 48 for respectively controlling the power source to lamp 60 and the fluorescent lamp 62 for reflecting light off the optic background 58 and through the rocker tray support 26 and the sample handling tray 28 to illuminate only samples held on the handling tray 28 so that any agglutination in the samples can be detected. Timer means 68, speed control means 70, reflected lamp source control means 72 and reflected fluorescent lamp source means 74 are all situated on the front panel 16 and the FIG. 7 circuitry of the same includes switches 75-75-75-75, fuses 76-76-76-76, resistor 78 and transformer 80, as represented in the circuitry in FIG. 7.

With continuing reference to the drawings for the method of serology testing in operating the semi-automated agglutination viewer 10, reagents and test specimen are prepared in accordance with well known procedures in the art. Test slide(s) (not shown in the drawings) are placed on the snap-in transparent handling tray 28 or, if preferred, directly on the transparent rocker base 30 of the rocker tray support 26. The proper amount of reagent and test specimen is added to the slide(s) or to the rocker base 30. The reagents and specimens are subsequently mixed well with wooden stir sticks, or something comparable. Timer means 68 and speed control means 70 are subsequently set on the front panel 16, and the rocking mode of the rocker tray means 24 is then activated by speed control means 70. The agglutination viewer 10 will shut off automatically in order that the operator can subsequently observe for agglutination under transmitted fluorescent (at 74), reflected tungsten filament (at 72) or by use of the well known tungsten source tyndall effect.

Thus, by the practice of this invention, the viewer 10 will bring uniformity and reproducibility to laboratory serology testing. It may be used in conjunction with any serological agglutination indicator reagents such as polystysene latex, red blood cells, charcoal, bentonite, glass beads, and etc. These tests may be performed on blood serum or plasma, urine, spinal fluid, acites, synoval fluid or other body fluids as per the reagent kit manufacturer's instructions.

The agglutination viewer 10 will provide a clean wettable surface on which serology agglutination reactions may be performed. The viewer 10 will control the length of rotation (mixing) as well as provide a uniform and reproducible motion of rotation. Length of rotation can be controlled by the switch 75 at times means 68 and speed or rotation by the switch 75 at speed control means 70.

These aspects are extremely important for there are over 40 different types of serology agglutination kits available to the clinical laboratory. Each of these kits may use different agglutinating particles. The type of particl determines for the most part how it must be handled (mixed and read) for erroneous results may be obtained if reagents are not properly mixed. Since there is a standard accepted method of manual rotation taught to medical technologists for agglutination reactions, the agglutination viewer 10 of this invention will reproduce this rotation on each and every run.

The light source under which agglutination reactions are observed will be optimized and standardized. By reading a particular reaction under the incorrect light, the technologist may observe false positive or false negative reactions. Current practice is to read the reaction under normal laboratory lighting conditions which may vary widely from lab to lab.

The focal length and magnification at which agglutination reactions are observed will be standardized. This will further reduce the possibility of false positive or false negative results.

While the present invention has been described herein with reference to particular embodiments thereof, a latitude of modifications, various changes and substitutions are intended in the foregoing disclosure, and it will be appreciated that in some instances some feature of the invention will be employed without a corresponding use of other features without departing from the scope of the invention as set forth.

We claim:

1. A semi-automated agglutination viewer comprising a housing including a top and a front panel; and upright back bound to said housing; magnifying means mounted in retainer means attached essentially perpendicularly to said upright back for aiding viewing of any agglutination; rocker tray means rotatably supported by said housing within the top thereof; motor means including a shaft and encompassed by said housing; power source means electrically engaging said motor means to supply power to same for rotating said motor shaft; gear means connected to said motor shaft for rotational power take-off therefrom; and a rocker arm means attached to said rocker tray means and secured eccentrically to said gear means such as to vertically reciprocate the rocker arm means from rotary power take-off from the gear means to cause rocking of the tray means; a sample handling tray;

said rocker tray means comprises a rocker tray support having a rocker base having a pair of ears integrally bound to said rocker base and attaching the tray support to said housing, one of said pair of ears attaching said rocker arm means, said rocker tray support and said sample handling tray being constructed such that in operation the sample handling tray snaps into or snaps out of the rocker tray support, a pair of flexible lips protruding from said rocker base; and a rocker tray back defining a channel for receiving an edge of the sample handling tray when same is snapped into said rocker tray support, an essentially arcuate optic background means enclosed within and supported by said housing above said motor means and said gear means; a lamp means electrically engaging said power source means and supported within and by said housing; and a fluorescent lamp means positioned in the corner of the adjoining point of said upright back and said magnifying retainer means, said fluorescent lamp means electrically engaged to said power source means;

and a pair of light shields, one of which is situated over said lamp means and the other over said fluorescent lamp means.

2. The agglutination viewer of claim 1 additionally comprising a timer means electrically engaging the power source means and selectively engaging the motor means to control the length of rocking time of the tray means; a speed control means electrically engaging the power source means and also selectively engaging the motor means to control the speed with which the rocker tray moves in its rocking mode via the gear means and the rocking arm means, and a reflected lamp source control means and a reflected fluorescent lamp source means both electrically engaging the power source means for respectively controlling the power source to said lamp means and said fluorescent lamp means for reflecting light off the optical background means and through said rocker tray support and said sample handling tray to illuminate any samples held on said handling tray so that any agglutination in the samples can be detected.

3. The agglutination viewer of claim 2 additionally comprising fiber optics system means attached to said upright back.

4. The agglutination viewer of claim 3 wherein said timer means, speed control means, reflected lamp source control means and reflected fluorescent lamp source means are all situated on said front panel.

* * * * *